Figure 1:
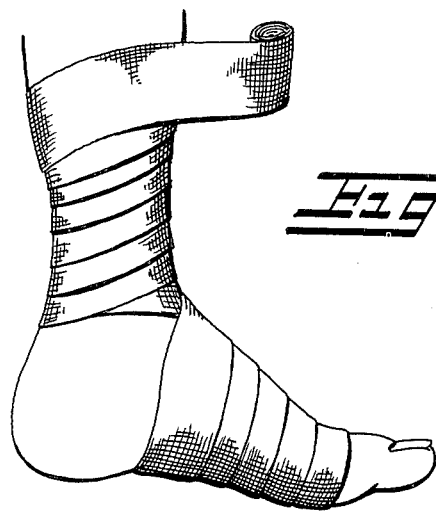

United States Patent [19]
Barnhardt

[11] 3,965,703
[45] June 29, 1976

[54] WARP KNITTED COMPRESSION BANDAGE FABRIC

[75] Inventor: J. David Barnhardt, Charlotte, N.C.

[73] Assignee: Southern Webbing Mills, Greensboro, N.C.

[22] Filed: Apr. 18, 1975

[21] Appl. No.: 569,587

[52] U.S. Cl. ................................................ 66/193
[51] Int. Cl.² ....................................... D04B 23/08
[58] Field of Search ............ 66/192, 190, 193, 195, 66/202

[56] References Cited
UNITED STATES PATENTS

| | | | |
|---|---|---|---|
| 2,150,133 | 3/1939 | Seidel | 66/192 X |
| 3,258,941 | 7/1966 | Formenti | 66/193 |
| 3,314,251 | 4/1967 | Bunger | 66/193 |
| 3,448,595 | 6/1969 | Baltzen | 66/193 |
| 3,570,482 | 3/1971 | Emoto et al. | 66/193 |
| 3,740,974 | 6/1973 | Bourgeois | 66/193 |
| 3,881,473 | 5/1975 | Corvi et al. | 66/193 X |
| 3,882,857 | 5/1975 | Woodall | 66/195 |

FOREIGN PATENTS OR APPLICATIONS

| | | | |
|---|---|---|---|
| 1,411,669 | 8/1965 | France | 66/193 |
| 1,055,741 | 4/1969 | Germany | 66/192 |

*Primary Examiner*—Ronald Feldbaum
*Attorney, Agent, or Firm*—Bell, Seltzer, Park & Gibson

[57] ABSTRACT

A ribbon-like bandage fabric which is stretchable in the lengthwise direction but substantially unstretchable in the widthwise direction. The fabric includes a plurality of walewise parallel stitch loop chains knit of stretchable yarn, a pair of filling yarns extending back and forth across the fabric and being held in the courses of the stitch loop chains, and elastic yarns inlaid in and extending along selected ones of the parallel stitch loop chains. This knit bandage fabric is lighter weight than conventional woven bandage fabric but has substantially the same elastic characteristics and may be produced in a more economical manner.

7 Claims, 4 Drawing Figures

U.S. Patent June 29, 1976 3,965,703

WARP KNITTED COMPRESSION BANDAGE FABRIC

This invention relates generally to a ribbon-like warp knitted compression bandage fabric and more particularly to such a fabric which includes a plurality of walewise parallel stitch loop chains knit of stretchable yarn with filling yarns extending back and forth across the fabric and being held in the stitch loop chain of each course of the fabric and including elastic yarns inlaid in and extending along selected ones of the parallel stitch loop chains.

Most commercially available stretchable ribbon-like compression bandage fabrics are of a woven construction which are woven on narrow fabric looms and at a relatively slow rate of speed. This type of ribbon-like bandage fabric is normally used to wrap or bind sprained or injured body joints and may be used for wrapping or binding the limbs to control excessive swelling. Because of the limited number of weaving constructions which may be woven, it is difficult to construct bandage fabrics having the desired degree of porosity and having the desired amount of stretch and fabric weight. Also, it is difficult to provide woven bandage material of various widths.

With the foregoing in mind, it is an object of the present invention to provide a ribbon-like warp knitted compression bandage fabric which is produced in an economical manner on a knitting machine and which fabric may be provided with the desired degree of porosity, the desired weight and the desired amount of stretchability for use in wrapping or binding various portions of the body.

In accordance with the present invention, the ribbon-like warp knitted compression bandage fabric is stretchable in the lengthwise direction but is substantially unstretchable in the widthwise direction. The fabric includes a plurality of walewise parallel stitch loop chains knit of stretchable yarn and forming successive courses extending from one side of the fabric to the other with filling yarn extending back and forth across the fabric and being held in the stitch loop chains and with an elastic yarn inlaid in and extending along selected ones of the parallel stitch loop chains. One filling yarn is positioned on one side of the inlaid elastic yarn and another filling yarn is positioned on the other side of the inlaid elastic yarn. The yarns used in knitting the bandage fabric are of sufficient size and character so that the weight of the fabric is within the range of about 185 to 350 grams per square yard. A two-inch width of the fabric will stretch to at least two times its unstretched relaxed length when a weight of 550 grams is applied thereto. The filling yarn is approximately six to eight times larger than the stretchable yarn forming the stitch loop chains. The knitted bandage fabric is lighter weight than a corresponding woven bandage fabric but has substantially the same elastic characteristics and has substantially the same appearance as a conventional woven bandage fabric.

Figure 4:
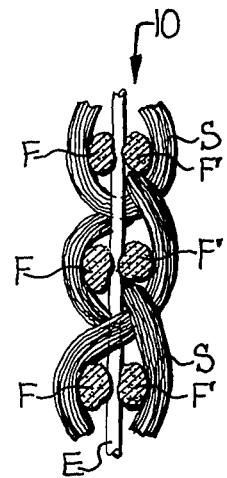
Figure 2:
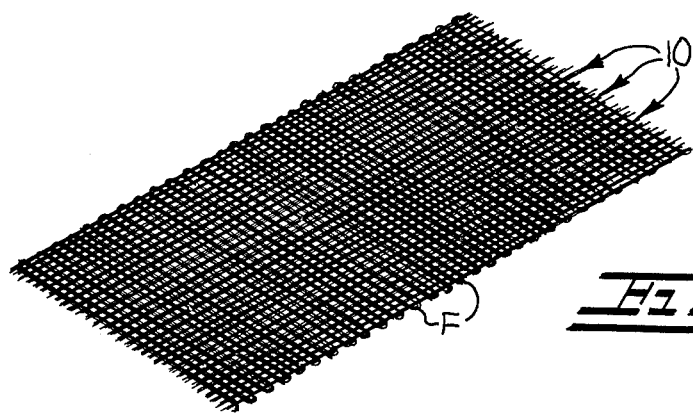
Figure 3:
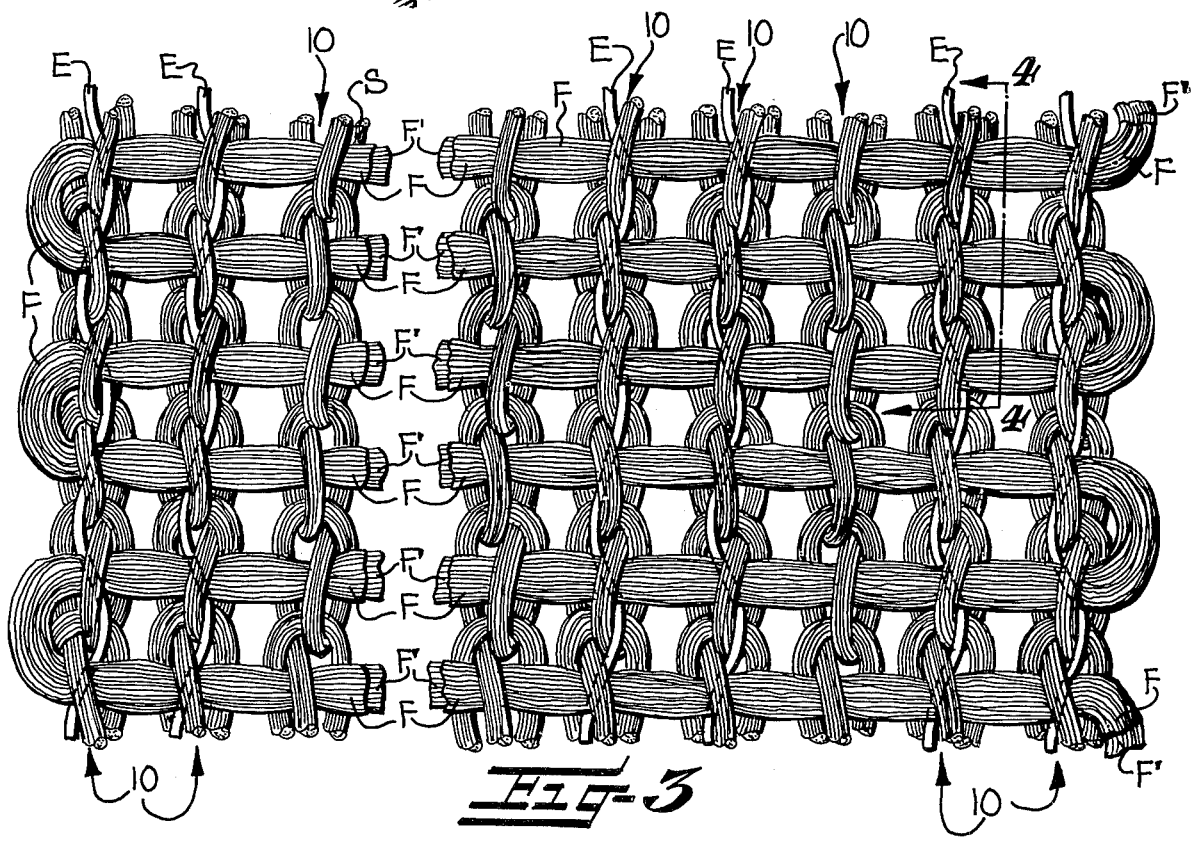

Other objects and advantages will appear as the description proceeds when taken in connection with the accompanying drawings, in which FIG. 1 illustrates the application of the warp knitted bandage fabric of the present invention to a foot and ankle;

FIG. 2 is a fragmentary isometric view of a small length of the present compression bandage fabric;

FIG. 3 is a greatly enlarged elevational view of a fragmentary portion of the fabric illustrated in FIG. 2, with a central portion broken away, and illustrating the manner in which the parallel stitch loop chains hold the filling yarns, and the manner in which the inlaid elastic yarn is incorporated in selected ones of the stitch loop chains; and FIG. 4 is a fragmentary vertical sectional view taken substantially along the line 4—4 in FIG. 3 to show the presence of the front and rear filling yarns on opposite sides of the inlaid elastic yarn.

The ribbon-like warp knitted compression bandage fabric of the present invention is stretchable in the lengthwise direction but is substantially unstretchable in the widthwise direction and is usually provided in widths of two-, three-, four- and six-inch rolls which may be 2½ to 3 feet long. As best shown in FIG. 3, the bandage fabric includes a plurality of walewise parallel stitch loop chains, broadly indicated at 10, which are knit of stretchable yarn S to form successive courses extending transversely of the fabric. The relaxed fabric preferably contains from about 10 to 18 stitch loop chains per inch of width and contains at least about 30 courses per inch in length.

Filling yarn F extends back and forth across the fabric and is held in the stitch loop chains of each of the courses. The filling yarn is substantially larger than the stretchable yarn S and is crimped to provide bulk but is substantially unstretchable. An elastic yarn E is inlaid in and extends along selected ones of the parallel stitch loop chains 10. The elastic yarn E may be of any suitable natural or synthetic material, such as rubber, elastomer or spandex and is preferably laid in the fabric in uncovered or raw condition. The manner in which the filling yarn F is incorporated in each course of the fabric and extends back and forth is clearly illustrated in FIG. 3 and it is preferred that one filling yarn, indicated at F in FIG. 4, extends back and forth across the fabric and on one side or in front of the inlaid elastic yarn E while a second filling yarn, indicated at F' in FIG. 4, extends across the fabric and on the other side or in back of the inlaid elastic yarn E. Both the first and second filling yarns F and F' are held in position in each course of the fabric and between the stitch loops on the face of the fabric and the laps of the stretchable yarn S on the rear side of the fabric.

Although the inlaid elastic yarn E may be incorporated in each parallel stitch loop chain 10, it is preferred that the elastic yarn E be incorporated in a pair of adjacent parallel stitch loop chains and be omitted from single stitch loop chains adjacent each side of the pair of stitch loop chains in which the elastic yarn E is inlaid. Thus, as illustrated in FIG. 3, the elastic yarn E is inlaid in a pair of parallel stitch loop chains at each selvage edge of the fabric and then is alternately omitted from a single stitch loop chain and incorporated in a pair of adjacent parallel stitch loop chains throughout the width of the fabric.

When the fabric is knitted with a width of two inches, it includes approximately 35 stitch loop chains 10 across the width thereof and the elastic inlaid yarn is uncovered and in the range of about 140 to 420 denier. The stretchable yarn S forming the parallel stitch loop chains 10 is a textured synthetic yarn, such as nylon, within the range of about 100 to 300 denier. The first and second filling yarns F and F' are approximately 6 to 8 times larger in total denier than the stretchable yarn S and the total denier of the filling yarns F and F′ is in the range of about 600 to 2400 denier.

It is to be understood that a wide variety of sizes and types of yarns may be used in knitting the compression bandage fabric of the present invention. To aid in understanding of the present invention, a specific but non-limiting example will be given of a particular compression bandage fabric which has been found to be satisfactory. This particular fabric will be described as it is knit on a Comez knitting machine having a flatbed of horizontally movable latch needles. However, it is to be understood that the present fabric may be knit on other types of knitting machines.

A plurality of ribbon-like bandage fabrics are knitted across the width of the knitting machine and the machine contains fourteen needles per inch. Stretchable textured yarns S of 150 denier are fed through the usual chain stitch guides which are shifted back and forth following each knitting stroke to form successive courses of stitch loops in the parallel stitch loop chains of the fabric, as illustrated in FIG. 3. An uncovered spandex yarn of 140 denier is fed through guides and to selected needles, the two adjacent needles at the outermost edges of the fabric, and to pairs of adjacent needles which are spaced apart by a single needle throughout the remainder of the width of the fabric. Three ends of 150 denier crimped and bulked filling yarns (a total of 450 denier) are fed to respective front and rear laying-in fingers which traverse the width of the fabric following each knitting stroke to lay in the first and second filling yarns F and F′ on the front and rear or opposite sides of the inlaid elastic yarn E.

When the fabric is removed from the machine and relaxed, there are approximately 16 stitch loop chains 10 for each inch of width or approximately 35 stitch loop chains across the two-inch width of the fabric and there are approximately 30 courses per inch. With these particular sizes of yarns, the fabric weighs approximately 190 grams per square yard and a weight of 550 grams is required to stretch the two-inch width fabric to a length of two times its unstretched relaxed length.

The fabric illustrated in FIG. 3 is formed with straight or parallel stitch loop chains 10, each of which is formed from a single yarn so that the adjacent stitch loop chains are connected together only by the filling yarns F and F′. However, it is to be understood that other types of warp knit construction may be employed and the stitch loop chain yarns may be shogged or lapped back and forth between adjacent chains. Also, more than one single yarn may be knit in each of the stitch loop chains to provide a non-raveling or non-run construction.

As has been stated, the width of the ribbon-like warp knitted compression bandage fabric of the present invention may be varied as desired. The fabric may be cut into suitable lengths and sold in rolls to facilitate application of the bandage to the joint or limb to be wrapped. The bandage material may be applied under any desired degree of stretch so that it applies the desired degree of compression to the part of the body to which it is applied.

In the drawings and specification there has been set forth a preferred embodiment of the invention, and although specific terms are employed, they are used in a generic and descriptive sense only and not for purposes of limitation.

That which is claimed is:

1. A ribbon-like warp knitted compression bandage fabric, said bandage fabric being stretchable in the lengthwise direction, but substantially unstretchable in the widthwise direction, said bandage fabric comprising
    a. a plurality of walewise parallel stitch loop chains knit of textured stretchable yarn within the range of about 100 to 300 denier and forming successive courses, said relaxed fabric containing from about 10 to 18 stitch loop chains per inch of width and containing at least about 30 courses per inch of length,
    b. filling yarn extending back and forth across said fabric and being held in each of said courses of said stitch loop chains, said filling yarn being approximately 6 to 8 times larger than said stretchable yarn and being crimped and substantially unstretchable, and
    c. an elastic yarn within the range of about 140 to 240 denier and inlaid in and extending along pairs of adjacent parallel stitch loop chains, and being omitted from single stitch loop chains throughout the medial portion of said fabric.

2. A bandage fabric according to claim 1 wherein said filling yarn (b) includes first filling yarn extending across said fabric and on one side of said inlaid elastic yarn, and second filling yarn extending across said fabric, and on the other side of said inlaid elastic yarn.

3. A bandage fabric according to claim 1 wherein each of said stitch loop chains is separate from adjacent stitch loop chains and is connected thereto only by said filling yarns.

4. A bandage fabric according to claim 1 wherein the weight of the fabric is within the range of about 185 to 350 grams per square yard.

5. A bandage fabric according to claim 1 being capable of lengthwise extension to a length of at least two times its unstretched relaxed length when a weight of 550 grams is applied to a two inch width thereof.

6. A bandage fabric according to claim 1 wherein said fabric is approximately 2 inches wide and includes approximately 35 of said parallel stitch loop chains across the width thereof.

7. A bandage fabric according to claim 1 wherein said stretchable yarn is 150 denier, said elastic yarn is 140 denier, and said filling yarn is 900 denier.

* * * * *